(12) United States Patent
Yoon et al.

(10) Patent No.: US 9,662,442 B2
(45) Date of Patent: May 30, 2017

(54) LINEAR FLOW REGULATING APPARATUS FOR INTRAVENOUS INFUSION

(71) Applicant: KOREA INSTITUTE OF MACHINERY & MATERIALS, Daejeon (KR)

(72) Inventors: Eui-Soo Yoon, Daejeon (KR); Moo-Ryong Park, Daejeon (KR); Bum Seog Choi, Daejeon (KR); Jun Young Park, Daejeon (KR); Il-Su Yoo, Daejeon (KR); Jeong Min Seo, Daejeon (KR); Soon-Chan Hwang, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 0 days.

(21) Appl. No.: 14/004,209

(22) PCT Filed: Nov. 16, 2012

(86) PCT No.: PCT/KR2012/009763
§ 371 (c)(1),
(2) Date: Sep. 10, 2013

(87) PCT Pub. No.: WO2013/073907
PCT Pub. Date: May 23, 2013

(65) Prior Publication Data
US 2014/0243759 A1    Aug. 28, 2014

(30) Foreign Application Priority Data

Nov. 18, 2011   (KR) .................. 10-2011-0120839

(51) Int. Cl.
*A61M 5/00*   (2006.01)
*A61M 5/168*  (2006.01)
(Continued)

(52) U.S. Cl.
CPC ...... *A61M 5/16813* (2013.01); *A61M 5/1407* (2013.01); *A61M 5/16881* (2013.01);
(Continued)

(58) Field of Classification Search
CPC .......... A61M 5/13813; A61M 5/16877; A61M 5/16881; A61M 39/287; A61M 2206/11;
(Continued)

(56) References Cited

U.S. PATENT DOCUMENTS 3,868,973 A * 3/1975 Bierman et al. ................ 138/43
4,361,147 A * 11/1982 Aslanian et al. ............... 604/33
(Continued)

FOREIGN PATENT DOCUMENTS

CN        23G85 7        3/2000
CN        201921250      8/2011
(Continued)

OTHER PUBLICATIONS

PCT Search Report & Written Opinion of PCT/KR2012/009763 (Mar. 28, 2013).
(Continued)

*Primary Examiner* — Edelmira Bosques
*Assistant Examiner* — Leah Swanson
(74) *Attorney, Agent, or Firm* — Hauptman Ham, LLP (57) ABSTRACT

The present invention relates to a linear flow regulating apparatus for intravenous infusion, and more particularly, to a flow regulating apparatus which is used in an infusion set for intravenous infusion to regulate the flow rate of a solution injected into a body. To eliminate the difficulties caused by the nonlinearity of conventional flow regulating apparatuses, which regulate flow rates by pressing a solution flow tube to adjust the flow passage area, the linear flow regulating apparatus has a control unit to be put in or taken out along the width of a flow channel unit through which the
(Continued)

solution flows when the height and length of the flow channel unit are fixed, and is capable of linearly regulating the flow rate by varying the flow passage area of the flow channel unit by adjusting the width of a flow channel unit.

6 Claims, 7 Drawing Sheets

(51) Int. Cl.
*A61M 5/14* (2006.01)
*A61M 39/28* (2006.01)
*F16K 5/04* (2006.01)

(52) U.S. Cl.
CPC .......... *A61M 5/141* (2013.01); *A61M 39/287* (2013.01); *A61M 2206/11* (2013.01); *F16K 5/0414* (2013.01)

(58) Field of Classification Search
CPC .. A61M 5/16813; A61M 5/141; A61M 25/00; A61M 25/0021; A61M 25/0023; A61M 39/00; A61M 39/28; A61M 39/281; A61M 39/283; A61M 39/285–39/288; A61M 2039/082; A61M 2039/085; A61M 2039/087; A61M 2205/3334
USPC ........................................ 604/246, 249, 250
See application file for complete search history.

(56) References Cited

U.S. PATENT DOCUMENTS

| | | | | |
|---|---|---|---|---|
| 4,702,397 A | * | 10/1987 | Gortz ................... | A61M 5/152 222/211 |
| 5,098,409 A | * | 3/1992 | Stock .................. | A61M 5/1684 128/DIG. 12 |
| 6,929,236 B1 | * | 8/2005 | Height ................ | A61M 39/286 137/553 |
| 2002/0061375 A1 | * | 5/2002 | Cartledge ............. | A61M 39/08 428/36.9 |
| 2002/0107472 A1 | | 8/2002 | Thompson | |

FOREIGN PATENT DOCUMENTS

| | | |
|---|---|---|
| DE | 522920 | 4/1931 |
| EP | 0456871 | 11/1991 |
| EP | 1360973 | 11/2003 |
| JP | 50-44863 | 4/1975 |
| KR | 10-2003-0014823 | 2/2003 |
| KR | 10-0870440 | 11/2008 |
| KR | 10-2010-0007015 | 1/2010 |
| KR | 10-1058539 | 8/2011 |
| KR | 10-2011-0115931 | 10/2011 |
| KR | 20-2011-0009910 | 10/2011 |
| KR | 10-2011-0130095 | 12/2011 |

OTHER PUBLICATIONS

Jae-Hoon Kim et al. "A Report for the Research about the Accuracy of a flow Regulator" The Korean Society of Emergency Medicine Journal, vol. 19, No. 1, (Feb. 2008).

Extended European Search Report, European Patent Office, Aug. 11, 2015, EP Application No. 12850257.2.

* cited by examiner

LINEAR FLOW REGULATING APPARATUS FOR INTRAVENOUS INFUSION

CROSS-REFERENCE TO RELATED APPLICATION

This application claims priority to and the benefit of Korean Patent Application No. 10-2011-0120839 filed in the Korean Intellectual Property Office on Nov. 18, 2011 and PCT Application No. PCT/KR2012/009763 filed in the Korean Intellectual Property Office on Nov. 16, 2012, the entire contents of which are incorporated herein by reference.

BACKGROUND OF THE INVENTION (a) Field of the Invention

The present invention relates to a flow regulating apparatus used for an intravenous infusion set (IV set), and more particularly to, a linear flow regulating apparatus which is capable of linearly regulating the flow rate of an infusion solution.

(b) Description of the Related Art

Figure 1:
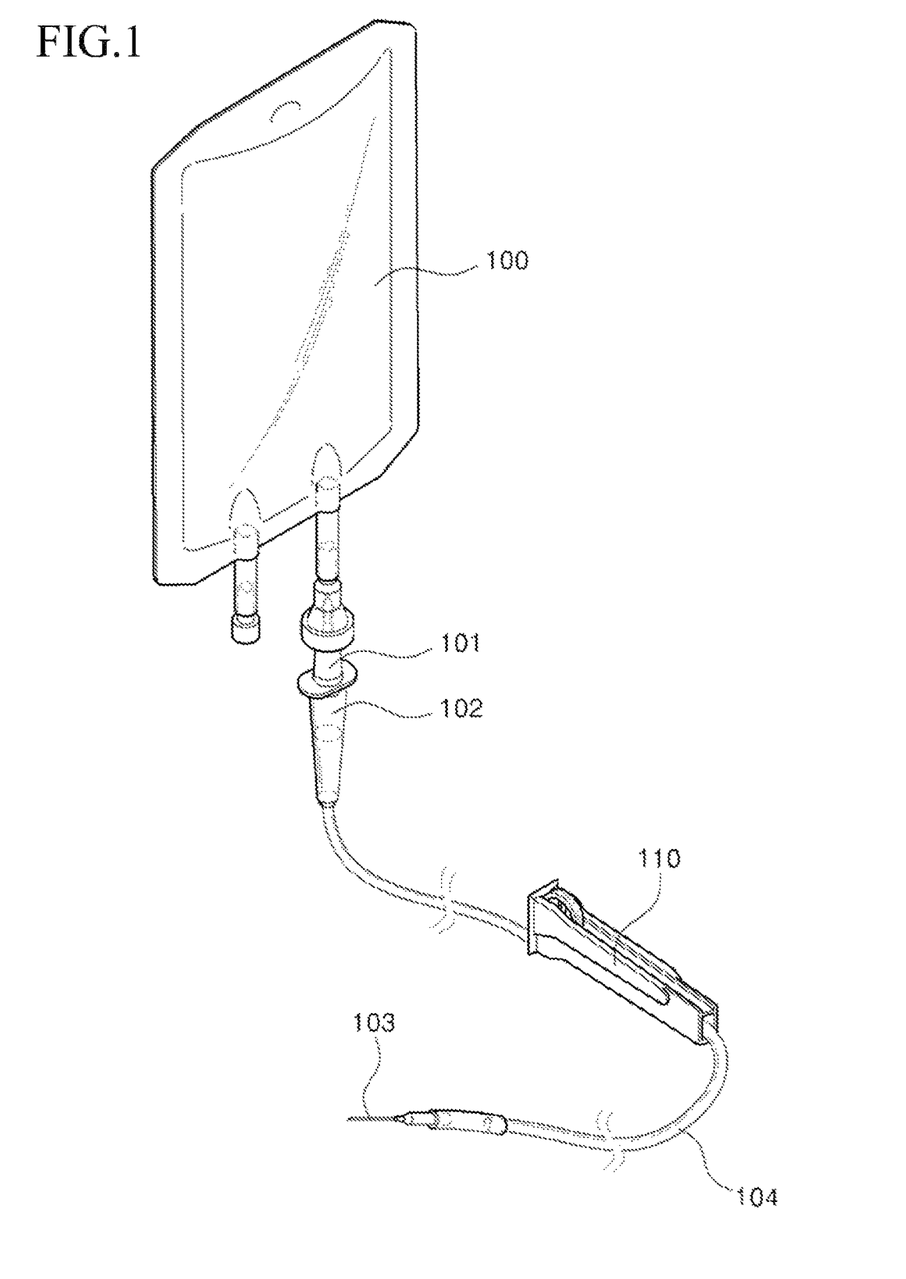
FIG. 1 is a perspective view showing an example of a conventional infusion solution bag.

As shown in FIG. 1, an intravenous injection system for intravenous administration of fluids includes an infusion solution bag 100 containing an infusion solution, an insertion spike 101 adapted to be inserted through a sealing plug of the infusion solution bag 100 to allow the infusion solution to be flown out from the infusion bag 100, a drip chamber 102 fixed to the lower end of the insertion spike 101 so that the infusion solution can fall in drops (counted in a unit of gtt) within the drip chamber 102, an injection needle 103 adapted to be inserted into a vein, a connecting tube 104 for interconnecting the drip chamber 102 and the injection needle 103 to serve as an infusion passage for the infusion solution, and an infusion flow regulator 110 mounted in the middle of the connecting tube 104 to be capable of regulating the flow rate of the infusion solution.

In general, the insertion spike 101, the drip chamber 102, the injection needle 103, the connecting tube 104, and the infusion flow regulator 110 are fabricated in one set, wherein the set fabricated in this manner is referred to as an infusion set. After the infusion solution in the infusion solution bag 100 connected to the infusion set is completely infused to a patient, only the empty infusion bag 100 may be replaced by a new one containing the same infusion solution if it is necessary to continuously inject the infusion solution to the patient. In addition, the insertion spike 101 and the drip chamber 102 are fabricated to make each of the drops of the infusion solution fall within the drip chamber 102 in the form of a water drop with a predetermined volume. For example, if they are fabricated to form 20 drops per 1 cc of the infusion solution, the volume of one drop will be 1/20 cc. Therefore, if the drops' falling interval within the drip chamber 102 is measured, it is possible to calculate the flow rate of the infusion solution injected through the infusion set.

For injecting an infusion solution to a patient, the flow rate of the infusion solution is prescribed in consideration of the type of the infusion solution, the kinds of agents mixed in the infusion solution, the condition of the patient, the kind of the disease of the patient, and the infusion flow regulator 110 is tuned so as to allow the infusion solution to be injected with the prescribed flow rate.

Regulating the flow rate of the infusion solution is very important since a medical accident may occur if the flow rate of the infusion solution being infused is not matched to the prescribed flow rate. Such an infusion flow regulator 110 has a manipulation unit 111 for regulating the cross-sectional area for passage of the infusion solution through the connecting tube 104, so that the flow rate of the infusion solution can be regulated by manipulating the manipulation part 111.

Figure 2:
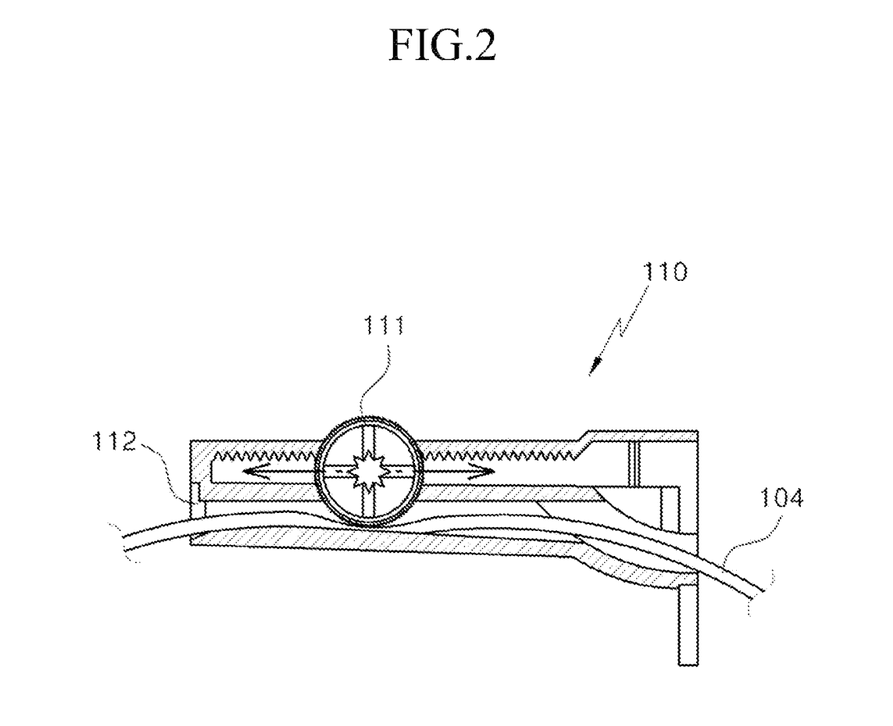
FIG. 2 is a front cross-sectional view showing an example of the structure of a conventional roller clamp type infusion flow regulator shown in FIG. 1.
Figure 3:
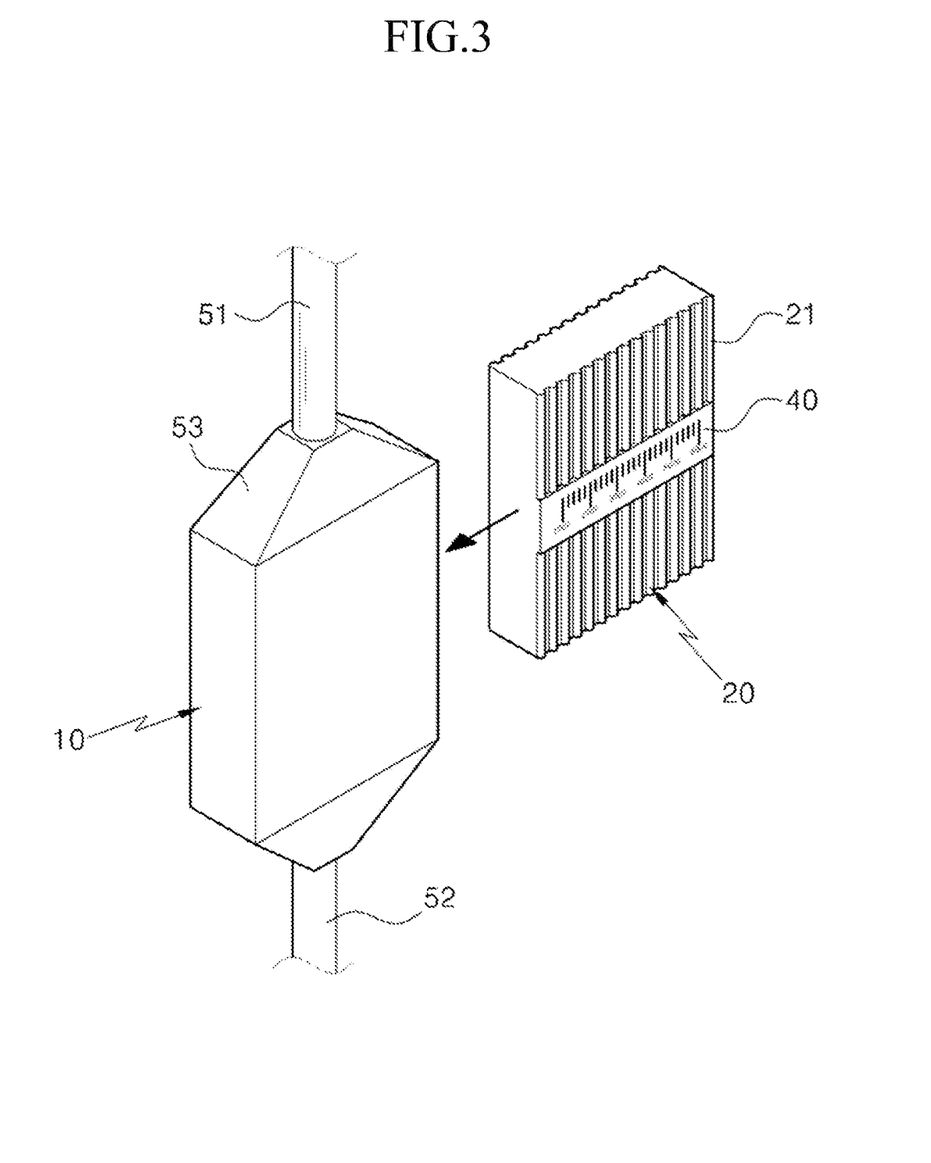
FIG. 3 is an exploded perspective view showing a linear flow regulating apparatus for intravenous infusion in accordance with the present invention.

The conventional infusion flow regulator 110 shown in FIG. 2 is a so-called "roller clamp" type infusion regulator, in which the manipulation unit 111 is formed in a roller type. Referring to the infusion flow regulator 110 in more detail, a connecting tube 104 is inserted through a recess 112 having opened top and bottom ends, and then the manipulation unit 111 adapted to press the connecting tube 104 is guided upward and downward. Since the depth of the recess 112 is gradually reduced toward the lower end, and hence the connecting tube 104 is pressed more and more as the manipulation unit 111 is moved more and more to the lower end of the recess 112. Thus, the flow rate of infusion fluid is regulated by measuring the flow rate at plural points while intermittently moving the manipulation unit 111, and by stopping the movement of the manipulation unit 111 when the flow rate reaches a desired level.

However, the roller clamp type infusion flow regulator 110 shown in FIGS. 1 and 2 is disadvantageous in that, since the flow rate should be measured while seeing the drip chamber 102 whenever the roller type manipulation unit 111 is moved, complicated measurements (drip rate counts) should be repeatedly performed, which will deteriorate the accuracy of flow rate regulation.

Moreover, the biggest problem of the conventional roller clamp type infusion flow regulator 110 is that it is difficult to regulate the flow rate. The conventional infusion flow regulator 110 regulates the flow rate by adjusting the flow passage area by pressing the connecting tube 104. Once the connecting tube 104 is pressed, the cross-section of the connecting tube 104 is deformed from a circular shape to an elliptical shape, and the cross-sectional area and the hydraulic radius of the connecting tube 104 become smaller, thus resulting in a flow reduction.

According to the Hagen-Poiseuille equation (Hagen-Poiseuille law in pipe) shown in the following Equation 1, which assumes that a flow in a cylindrical tube is steady and laminar, the velocity profile of a fluid flowing within the tube is parabolic, and the flow rate of the fluid is inversely proportional to the length of the tube and proportional to the fourth power of the radius. This results in nonlinear flow regulation, and therefore it is difficult to accurately regulate the flow rate merely by varying the length or radius of the cylindrical tube.

$$Q = \frac{\Delta p \pi r_0^4}{8 \mu l} \qquad \text{Equation 1}$$

(where Q is the flow rate, $r_0$ is the radius of the tube, l is the length of the tube, $\mu$ is the viscosity of the fluid, and $\Delta p$ is the pressure difference in the tube.)

As above, regulating the flow rate by variations in diameter and length is nonlinear and complex even in the cylindrical tube having quite a simple structure. Moreover, variations in the cross-sectional area and length of the flow passage are even more complicated in the roller clamp type flow regulator, making flow regulation more difficult.

Further, the conventional infusion flow regulator 110 includes the above-mentioned roller clamp type flow regulator, a cylindrical rotary flow regulator, a clock-type flow regulator, a constant infusion pump, etc. Although the roller clamp type flow regulator can vary the flow passage area by a roller, it is not capable of uniformly adjusting the dimension, shape, hydraulic radius, etc of the flow passage area. Therefore, the roller clamp type flow regulator has the drawbacks that it is difficult to regulate the flow rate by the above-mentioned Equation 1, the roller for manipulation is easily moved at a fixed position, and a creep may occur in a deformed tube over time, causing a change in flow rate.

The rotary flow regulator has a constant cross-sectional area, and is adapted to regulate flow rate by adjusting the length (which is proportional to the angle of rotation) of a capillary tube by turning the dial. The rotary flow regulator also has the problem that it is difficult to regulate the flow rate according to the above-mentioned Equation 1 (the scale is nonlinear because the flow rate is inversely proportional to the length l of the capillary).

In addition, the constant infusion pump has the problems that it is not convenient to install and use it due to its large size, and runs a high risk of contamination because it is used on many people.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a linear flow regulating apparatus for intravenous infusion used in an infusion set or the like for injecting a solution, which has a control unit to be put in or taken out along the width of a flow channel unit through which the solution flows when the height and length of the flow channel unit are fixed, and is capable of linearly regulating the flow rate within the flow channel unit, in proportion to the width, by varying the flow passage area by adjusting the width of the flow channel unit.

The other objects and advantages of the present invention will be described below and become more apparent by describing exemplary embodiments thereof. Further, the objects and advantages of the present invention will be achieved by elements and a combination of the elements disclosed in the claims.

An exemplary embodiment of the present invention provides a linear flow regulating apparatus for intravenous infusion, the apparatus including: a flow channel unit having a rectangular cross-section that allows a solution to flow therethrough; and a control unit that is adapted to be put in or taken out of one side of the flow channel unit to vary the flow passage area of the flow channel unit, wherein the control unit may vary the flow passage area while moving along the width of the flow channel unit so as to linearly regulate the flow rate of the solution.

The linear flow regulating apparatus may further include a fine adjustment unit that is formed at a contact region between the flow channel unit and the control unit to adjust the moving distance of the control unit along the width.

The fine adjustment unit may include: a plurality of protruding parts formed on an inner peripheral surface of the flow channel unit; and a plurality of coupling parts formed on the outer peripheral surface of the control unit so as to engage the protruding parts.

A gauge may be formed on one surface of the control unit to check the flow rate of the solution varying with the flow passage area of the flow channel unit when the control unit is put in or taken out.

The flow channel unit may include: an inlet tube connected at the front end to allow the solution to simultaneously flow in over the entire width of the flow channel unit; and an outlet tube connected at the rear end to allow the solution to simultaneously flow out over the entire width of the flow channel unit.

The flow channel unit may further include a pinion adjustment unit that is rotatable in meshing engagement with the plurality of coupling parts formed on the outer peripheral surface of the control unit, wherein the control unit may be put into or taken out of one side of the flow channel unit by rotating the pinion adjustment unit.

The pinion adjustment unit may include: a pinion part meshing with the coupling parts; and a fixing part for fixing the pinion part to the outer peripheral surface of the flow channel unit.

As discussed above, the linear flow regulating apparatus for intravenous infusion in accordance with the present invention has the advantage of enabling accurate flow regulation by linearly regulating the flow rate of a solution. The present invention makes it possible to quickly and accurately regulate the flow rate to a desired level by calibrating the number of drops from a drop chamber once, since the flow rate of the solution is maintained linear.

Moreover, the present invention has the advantage of simple configuration and ease use because the control unit is configured to be put in or taken out along the width of the flow channel unit.

Further, the present invention has the advantage of cutting down production costs, increasing production yield, and reducing costs incurred during production.

DETAILED DESCRIPTION OF THE EMBODIMENTS

Before exemplary embodiments of the present invention are described in detail, it will be understood that, detailed constitution and arrangements of elements described in the detailed description or illustrated in the drawings should not be construed as limiting the application of the invention. The invention may be embodied in many alternate forms and performed in various methods.

The terms or words to describe the direction of an apparatus or element (for example, "front", "back", "up", "down", "top", "bottom", "left", "right" and "lateral", among others) are used to simplify the description of the invention. It will be, therefore, understood that these terms do not mean that the relevant apparatus or element shall be only in the specific direction.

The present invention has the following features to attain the aspect mentioned above.

The present invention will now be described more fully hereinafter with reference to the accompanying drawings, in which preferred embodiments of the invention are shown. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Therefore, configurations described in embodiments and shown in drawings of the present specification indicate only the most preferred example rather than indicating all the technical ideas of the present disclosure and therefore, it is to be understood that various equivalents and modifications that can replace the above configurations may be present.

Hereinafter, a linear flow regulating apparatus for intravenous infusion in accordance with an exemplary embodiment of the present invention will be described in detail with reference to FIGS. 1 to 7.

Figure 4:
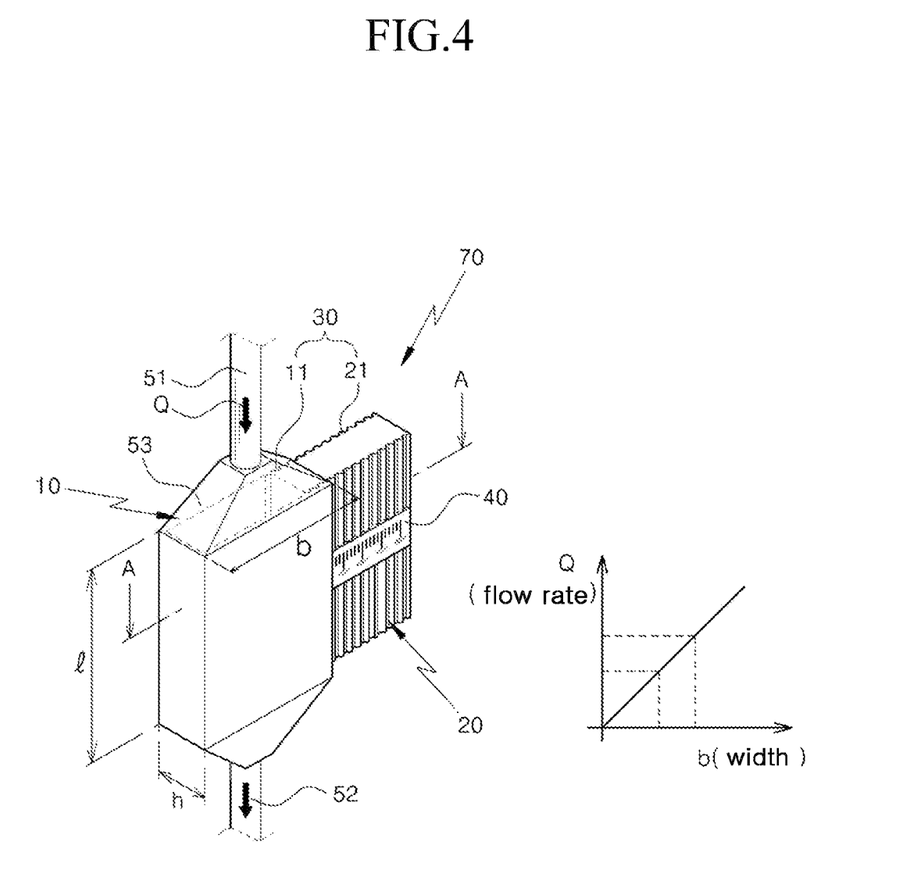
FIG. 4 is a perspective view of FIG. 3.

Referring to FIG. 4, the linear flow regulating apparatus 70 for intravenous infusion according to the present invention includes a flow channel unit 10, a control unit 20, a fine adjustment unit 30, and a gauge 40.

The flow channel unit 10 is hollow inside, and its front and rear ends have an open rectangular cross-section. In the present invention, the height of the flow channel unit 10 is denoted by 'h', its length is denoted by 'l', and its width is denoted by 'b', where the width b is much greater than the height (b>>h), making the flow channel unit 10 in a rectangular shape.

By ignoring end wall effects, the Hagen-Poiseuille law in channel can be applied as shown in the following Equation 2.

$$Q = \frac{\Delta p h^3 b}{12 \mu l} \qquad \text{Equation 2}$$

(where Q is the flow rate, Δp is the pressure difference in the channel (flow channel unit 10), h is the height of the channel, b is the width of the channel, μ is the viscosity of the fluid, and l is the length of the channel.)

That is, it can be seen that, while adjusting the area by pressing the conventional connecting tube 104, as shown in FIG. 2 depicting the conventional infusion flow regulator, does not contribute to linear regulation of flow rate by Equation 1 set forth in [Background of the Invention], the flow rate in the flow channel unit 10 having a rectangular cross-section is inversely proportional to the length l, proportional to the third power of the height h, and linear to the width b.

According to the present invention, the height h and length l of the flow channel unit 10 are fixed and the width b of the flow channel unit 10 is adapted to be controlled by the control unit 20 to be described later. Therefore, the flow rate can be linearly and accurately regulated by controlling the width b of the flow channel unit 10, which is linear to the flow rate (Q (flow rate) ∝ b (width)).

Moreover, an inlet tube 51 and an outlet tube 52 are connected at the open front and rear ends of the flow channel unit 10 so as to allow a solution N to flow therethrough. The inlet tube 51 is disposed at the front end of the flow channel unit 10, and the outlet tube 52 at the rear end of the flow channel unit 10, so that the solution flowing from the inlet tube 51 migrates to the outlet tube 52 through the inside of the flow channel unit 10.

An expanding or contracting tube portion 53 is formed such that ends of the inlet tube 51 and outlet tube 52 having a circular cross-section respectively correspond to the front and rear ends of the flow channel unit 10 communicating with each other. Thus, the solution entering from the inlet tube 51 simultaneously flows in over the entire width b of the front end of the flow channel unit 10.

Also, the solution flowing out through the inlet tube 51 and the flow channel unit 10 simultaneously exits over the entire width b of the rear end of the flow channel unit 10.

Figure 5:
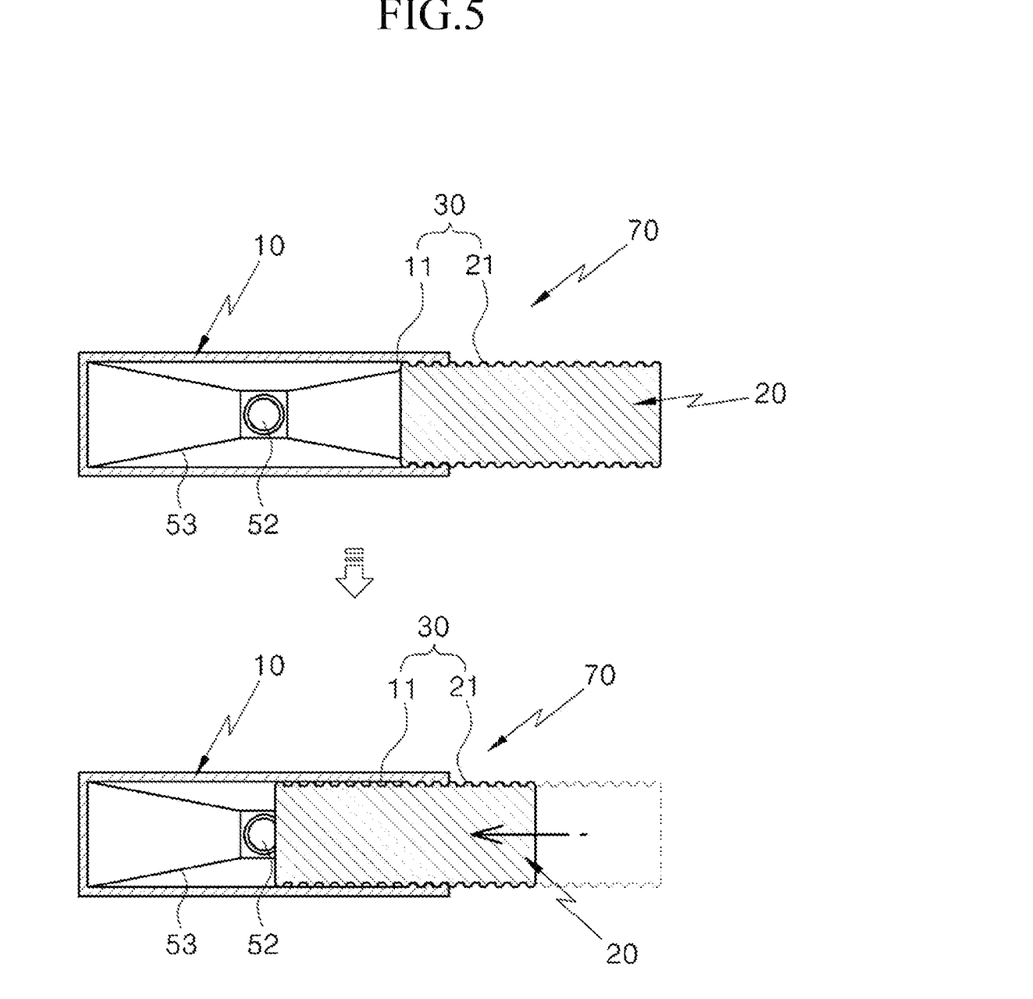
FIG. 5 is a view taken along the line A-A of FIG. 4
Figure 6:
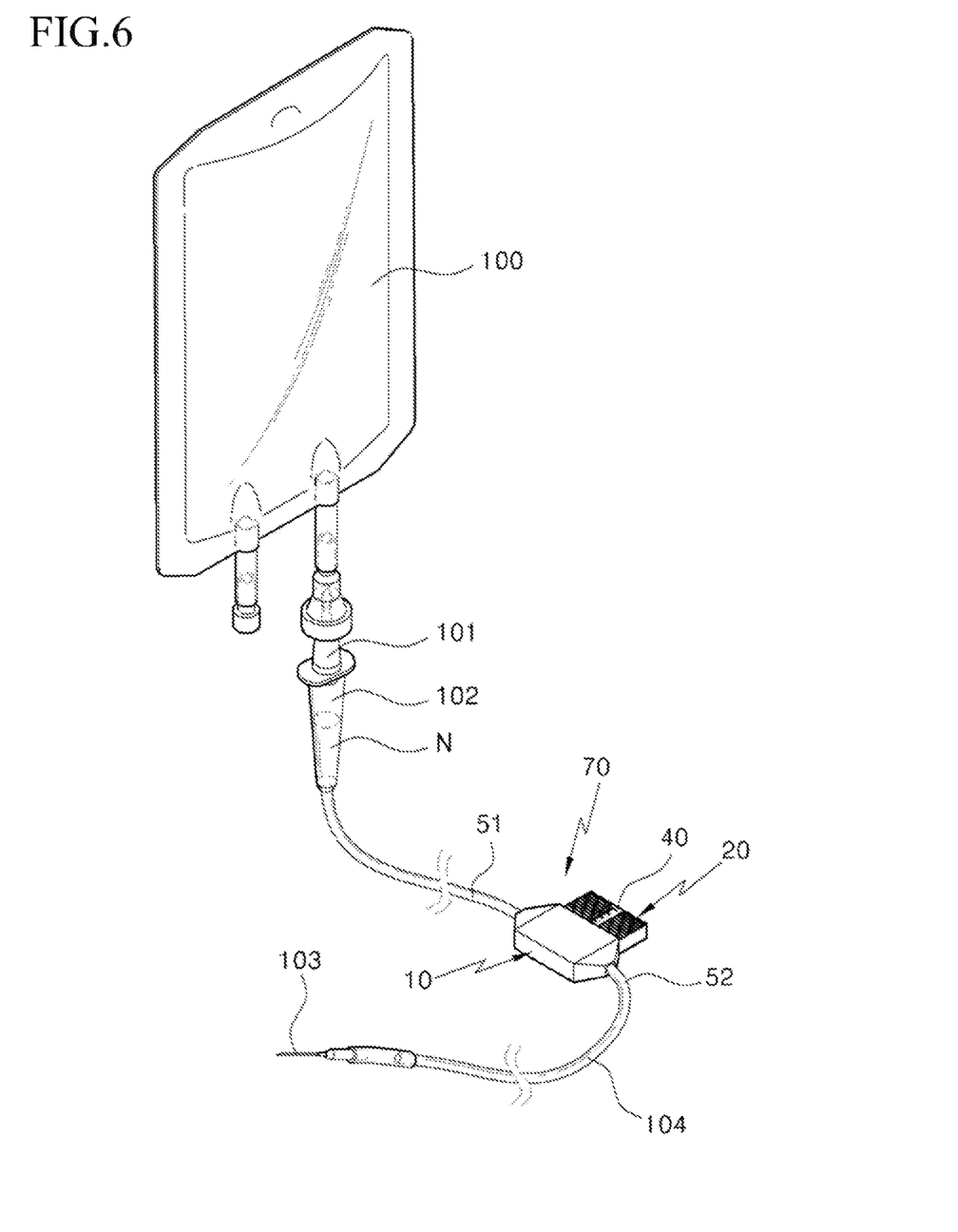
FIG. 6 is a perspective view showing an infusion set to which a linear flow regulating apparatus for intravenous infusion in accordance with an exemplary embodiment of the present invention.

Referring to FIG. 5, the control unit 20 is configured to be inserted into one side of the flow channel unit 10, and has a rectangular cross-sectional shape corresponding to the flow channel unit 10.

With this configuration, the control unit 20 may be put in or taken out along the width b of the flow channel unit 10 by the user, when the control unit 20 is inserted corresponding to one side of the flow channel unit 10.

That is, as the flow passage area of the flow channel unit 10 decreases when the control unit 20 is put in, and the flow passage area of the flow channel unit 10 increases when the control unit 20 is taken out (the flow channel unit 10 is not fully removed from the control unit 20), the flow rate in the flow channel unit 10 can be regulated.

In other words, the control unit 20 is inserted into one side of the flow channel unit 10 so as to correspond to and come in contact with the inside of the flow channel unit 10 whose height h and length l are fixed, whereby the flow rate of the solution through the flow channel unit 10 can be regulated while moving the control unit 20 along the width b of the flow channel unit 10.

Moreover, as the flow passage area of the flow channel unit 10 is linear (proportional) to the width b, as described above, the flow rate of the solution through the flow channel unit 10 of the present invention is linearly adjusted with the same amount as the width b of the flow channel unit 10. As a result, the linear flow regulating apparatus for intravenous infusion according to the present invention is able to accurately regulate the flow rate of an infusion solution when applied to an infusion set.

As described above, the fine adjustment unit 30 is for finely adjusting the moving distance of the control unit 20 put in or taken out along the width b of the flow channel unit 10.

The fine adjustment unit 30 includes protruding parts 11 and coupling parts 21.

The protruding parts 11 may consist of one or more protrusions protruding on an inner peripheral surface of the flow channel unit 10. If the protruding part 11 consists of two protrusions, the protrusions are spaced apart from each other on an inner peripheral surface of the flow channel unit 10.

The coupling parts 21 are formed on the outer peripheral surface of the control unit 20 so as to engage the protruding parts 11.

More specifically, as the control unit 20 is put into or taken out of one side of the flow channel unit 10, the above-described protruding parts 11 are formed along the width b (in the movement direction of the control unit 20) on a region contacting the outer peripheral surface of the control unit 20, i.e., on the inner peripheral surface of the flow channel unit 10, and the above-described coupling parts 21 are formed along the width b (in the movement direction of the control unit 20) on a region contacting the inner peripheral surface of the flow channel unit 10, i.e., on the outer peripheral surface of the control part 20.

If the plurality of coupling parts 21 formed on the control part 20 sequentially and bilaterally engage the protruding parts 11, like gears, and then the control unit 20 is put in along the width b of the flow channel unit 10, this means that the plurality of coupling parts 21 are inserted between some of the protruding parts 11 along the width b and then between another protruding parts 11 in a repetitive fashion.

That is, the moving distance of the control unit 20 along the width b is accurately adjusted as the distance between the protruding parts 11 or the distance between the coupling parts 21 changes (ex: a decrease or increase of 10 cc/hr each time the coupling parts 21 move one space), so that the flow passage area of the flow channel unit 10 can be accurately varied.

While the protruding parts 11 and the coupling parts 21 are configured to protrude outward, various changes can be made, including the protruding parts 11 configured to be put in and the coupling parts 21 configured to engage the protruding parts 11 in a male-female relation, according to a variety of exemplary embodiments, as long as the moving distance of the control unit 20 along the width b can be accurately and sequentially adjusted.

The gauge 40 is formed along the width b (in the movement direction of the control unit 20) on one surface of the control unit 20 that is put into or taken out of the flow channel unit 10. By checking a measurement on the gauge 40 corresponding to one edge of the flow channel unit 10 whenever the control unit 20 is put into or taken out of the flow channel unit 10 by means of the fine adjustment unit 30, the user is able to find the flow rate through the variable flow passage of the flow channel unit 10, based on the measurement on the gauge 40.

The gauge 40 has no protrusion, and serves to prevent a solution from migrating along the length l from the control unit 20 through the protruding parts 11.

Figure 7:
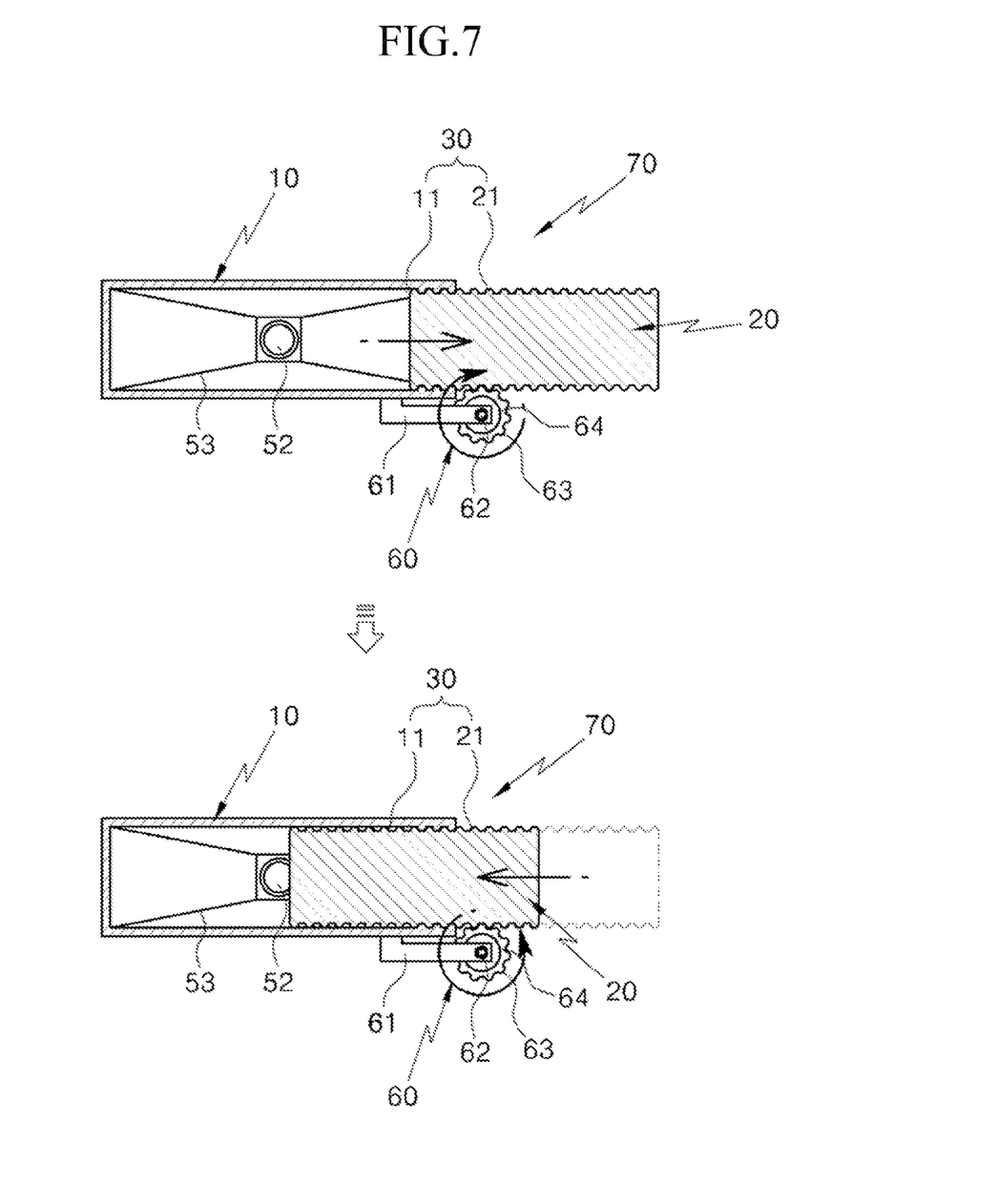
FIG. 7 is a planar cross-sectional view showing a pinion adjustment unit in accordance with an exemplary embodiment of the present invention.

Referring to FIG. 7, a pinion adjustment unit 60 includes a fixing part 61, one end of which being fixed to the outer peripheral surface of the flow channel unit 10 and the other end of which extending toward the control unit 20, a reference axis 62 formed at the center of a circular-shaped body, with the fixing part 61 being fixed to the reference axis 62, and a pinion part 64 having a plurality of gears 63 formed on the outer circumference, and meshing with the plurality of coupling parts 21 formed on the outer peripheral surface of the control unit 20.

That is, a plurality of gears 63 are formed on the outer circumference of the pinion part 64, and the gears 63 may mesh with the plurality of coupling parts 21 formed on the outer peripheral surface of the control unit 20.

In this case, the user may put or take the control unit 20 into or out of the flow channel unit 10 by directly pushing or pulling the control unit 20. Otherwise, the user may put or taken the control unit 20 into or out of the flow channel unit 10 in the rotating direction of the pinion part 64 by rotating the pinion part 64, because the gears 63 formed on the outer circumference of the pinion part 64 mesh with the coupling parts 21 of the control unit 20.

In other words, if the pinion adjustment unit 60 consisting of the fixing part 61 and the pinion part 64 is rotated counterclockwise, the gears 63 of the pinion part 64 push the control unit 20 toward the flow channel unit 10, thus causing the control unit 20 to be put into the flow channel unit 10.

On the contrary, if the pinion adjustment unit 60 is rotated clockwise, the gears 63 of the pinion part 64 pulls the control unit 20 outward of the flow channel unit 10, thus causing the control unit 20 to be taken out of the flow channel unit 10.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A linear flow regulating apparatus for an intravenous infusion set, the apparatus comprising:
    a flow channel unit having a rectangular cross-section, and a rectangular shaped flow passage area inside the flow channel unit so as to allow that allow a solution to flow therethrough;
    a control unit that is adapted to be put in or taken out of one side of the flow channel unit to vary a width of the flow passage area; and
    an adjustment unit that is formed at a contact region between the flow channel unit and the control unit to adjust a moving distance of the control unit along a width direction of the flow channel unit, wherein the width direction is transverse to a flow direction of the solution,
    wherein the control unit is configured to by uniformly decreasing the flow passage area of the flow channel unit by being inserted into the flow channel unit along the width of the flow channel unit towards an opposite side of the one side of the flow channel unit, and
    wherein the control unit is configured to regulate the flow rate of the solution to be linearly proportional to the width of the flow passage area.

2. The linear flow regulating apparatus of claim 1, wherein a gauge is formed on one surface of the control unit to check the flow rate of the solution varying with the flow passage area of the flow channel unit when the control unit is put in or taken out.

3. The linear flow regulating apparatus of claim 1, wherein the flow channel unit comprises:
    an inlet tube connected at a front end of the flow channel unit to allow the solution to simultaneously flow in over the entire width of the flow channel unit; and
    an outlet tube connected at a rear end of the flow channel unit to allow the solution to simultaneously flow out over the entire width of the flow channel unit.

4. The linear flow regulating apparatus of claim 1, wherein the adjustment unit comprises:
    a plurality of protruding parts formed on an inner peripheral surface of the flow channel unit; and
    a plurality of coupling parts formed on an outer peripheral surface of the control unit so as to engage the protruding parts.

5. The linear flow regulating apparatus of claim 4, wherein the flow channel unit further comprises a pinion adjustment unit that is rotatable in meshing engagement with the plurality of coupling parts formed on the outer peripheral surface of the control unit,
    wherein the control unit is put into or taken out of the one side of the flow channel unit by rotating the pinion adjustment unit.

6. The linear flow regulating apparatus of claim 5, wherein the pinion adjustment unit comprises:
    a pinion part meshing with the coupling parts; and
    a fixing part for fixing the pinion part to the outer peripheral surface of the flow channel unit.

\* \* \* \* \*